United States Patent
Drndic et al.

(10) Patent No.: US 10,017,813 B2
(45) Date of Patent: Jul. 10, 2018

(54) DIFFERENTIATION OF MACROMOLECULES AND ANALYSIS OF THEIR INTERNAL CONTENT IN SOLID-STATE NANOPORE DEVICES

(71) Applicant: The Trustees of The University of Pennsylvania, Philadelphia, PA (US)

(72) Inventors: Marija Drndic, Philadelphia, PA (US); Kimberly Elizabeth Venta, Philadelphia, PA (US); Gabriel Shemer, Jenkintown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 232 days.

(21) Appl. No.: 14/781,453

(22) PCT Filed: Mar. 26, 2014

(86) PCT No.: PCT/US2014/031863
§ 371 (c)(1),
(2) Date: Sep. 30, 2015

(87) PCT Pub. No.: WO2014/165372
PCT Pub. Date: Oct. 9, 2014

(65) Prior Publication Data
US 2016/0053313 A1    Feb. 25, 2016

Related U.S. Application Data

(60) Provisional application No. 61/808,459, filed on Apr. 4, 2013.

(51) Int. Cl.
G01N 27/447    (2006.01)
C12Q 1/6869    (2018.01)
G01N 33/487    (2006.01)

(52) U.S. Cl.
CPC ..... *C12Q 1/6869* (2013.01); *G01N 27/44743* (2013.01); *G01N 27/44791* (2013.01); *G01N 33/48721* (2013.01)

(58) Field of Classification Search
CPC .............................................. G01N 33/48721
See application file for complete search history.

(56) References Cited

U.S. PATENT DOCUMENTS

| | | | |
|---|---|---|---|
| 6,746,594 B2 | 6/2004 | Akeson et al. | |
| 2012/0142016 A1 | 6/2012 | Ronaghi et al. | |
| 2012/0234679 A1* | 9/2012 | Garaj ..................... | B82Y 30/00 204/520 |

(Continued)

FOREIGN PATENT DOCUMENTS

| WO | WO 2009/020682 A2 | 2/2009 |
|---|---|---|
| WO | WO 2011/103424 A2 | 8/2011 |
| WO | WO 2012/116161 A1 | 8/2012 |

OTHER PUBLICATIONS

Of Storm et al., "Fabrication of solid-state nanopores with single-nanometre precision," nature materials, vol. , Aug. 2003, pp. 537-540.*

(Continued)

*Primary Examiner* — Alexander S Noguerola
(74) *Attorney, Agent, or Firm* — Baker & Hostetler LLP

(57) ABSTRACT

Provided are solid-state nanopore platforms for fast, electronic, label-free and high-resolution analysis of biomolecules.

21 Claims, 10 Drawing Sheets

(56) References Cited

U.S. PATENT DOCUMENTS

2013/0180867 A1* 7/2013 Rosenstein ...... G01N 33/48721
205/777.5
2013/0256154 A1* 10/2013 Peng ...................... B82Y 30/00
205/780.5

OTHER PUBLICATIONS

Li et al., "Ion-beam sculpting at nanometer length scales." Nature, vol. 412 Jul. 12, 2001, pp. 166-169.*
Lv et al., "The Fluctuations of Blocked Ionic Current Reveal the Instantaneous Statuses of DNA in Graphene Nanopore," eprint arXiv:1302.3671, publication date Feb. 2013, 19 pages.*
Sigalov et al., "Detection of DNA Sequences Using an Alternating Electric Field in a Nanopore Capacitor," NanoLetters 2008 vol. 8, No. 1, 56-63.*
U.S. Appl. No. 13/587,141, filed Aug. 16, 2012, Drndic et al.
Rosenstein, et al., "Integrated Nanopore Sensing Platform with Sub-Microsecond Temporal Resolution", Nature Methods, May 2012, vol. 9(5), 487-494.
Wanunu, "DNA Translocation Governed by Interactions with Solid-State Nanopores", Biophysical Journal, Nov. 2008, vol. 95, 4716-4725.
Wanunu, "Nanopore Analysis of Individual RNA/Antibiotic Complexes", ACS Nano, Dec. 2011, vol. 5(12), 9345-9353.

\* cited by examiner

DIFFERENTIATION OF MACROMOLECULES AND ANALYSIS OF THEIR INTERNAL CONTENT IN SOLID-STATE NANOPORE DEVICES

CROSS-REFERENCE TO RELATED APPLICATION

This application is a National Stage Application filed under 35 U.S.C. 371 of International Application No. PCT/US2014/031863, filed Mar. 26, 2014, which claims the benefit of U.S. Provisional Application No. 61/808,459, "Differentiation Of Macromolecules And Analysis Of Their Internal Content In Solid-State Nanopore Devices", (filed Apr. 4, 2013), the entirety of which applications are incorporated by reference herein in their entireties for any and all purposes.

STATEMENT OF GOVERNMENT RIGHTS

This invention was made with government support under NSF MRSEC grants DMR-0520020 and DMR-1120901, NIH Grant R21HG004767, and by NSF NSEC grant DMR08-32802. The government has certain rights in the invention.

TECHNICAL FIELD

The present disclosure relates to the field of solid-state nanopore devices and to structural analysis of biomolecules.

BACKGROUND

Nanopores are a unique and powerful tool for a variety of single-molecule studies, including detection of miRNAs, discrimination between classes of nucleic acids, detection of protein-DNA binding, and measurement of molecular force. Another applications of nanopore measurements is in the field of DNA sequencing, but nanopores at present face challenges in spatial and temporal resolution. Accordingly, there is a need in the art for sensitive nanopores that have sufficient temporal resolution to resolve bases as they pass through the pore.

SUMMARY

In meeting the described challenges, the present disclosure first provides systems, the systems comprising: a membrane having a first region that defines a thickness in the range of from about 0.1 nm to about 10 nm; a pore formed in the first region of the membrane, the pore defining a cross-sectional dimension in the range of from about 0.5 nm to about 5 nm; a voltage source configured to, during operation, apply a voltage in the range of from about 0.1 V to about 2 V across the pore.

Also provided are methods of fabricating devices, comprising ablating material from a membrane so as to form a first thinned region of the membrane; determining, by current measurement, a first location or several first locations of the thinned region that defines a minimum thickness of the first thinned region; and ablating material at the first location of the first thinned region so as to give rise to a pore extending through the membrane.

Further disclosed are methods, comprising applying a voltage in the range of from about 0.1 V to about 2 V across a pore formed in a membrane, the pore defining a cross-sectional dimension in the range of from about 0.5 nm to about 5 nm, the voltage being applied so as to effect translocation of a molecule through the pore, the temperature at the environment proximate to the pore being between about 0 deg. C and about 25 deg. C.; and monitoring an amplified electronic signal related to the translocation of the molecule.

Additionally provided are methods, comprising applying a voltage in the range of from about 0.1 V to about 1.5 V across a pore formed in a membrane, the pore defining a cross-sectional dimension in the range of from about 0.5 nm to about 5 nm, the voltage being applied so as to effect translocation of a molecule through the pore, and; monitoring an amplified electronic signal related to the translocation of the molecule, the signal being in the range of from about 100 kHz to about 100 MHz.

BRIEF DESCRIPTION OF THE DRAWINGS

The summary, as well as the following detailed description, is further understood when read in conjunction with the appended drawings. For the purpose of illustrating the disclosed technology, there are shown in the drawings exemplary embodiments; however, the disclosure is not limited to the specific methods, compositions, and devices disclosed. In addition, the drawings are not necessarily drawn to scale or proportion. In the drawings.

DETAILED DESCRIPTION OF ILLUSTRATIVE EMBODIMENTS

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claims. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "approximately" or "about," it will be understood that the particular value forms another embodiment. All ranges are inclusive and combinable, and all documents cited herein are incorporated by reference in their entireties for any and all purposes.

It is to be appreciated that certain features of the disclosure which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one aspect, the present disclosure provides systems. The disclosed systems suitably include a membrane having a first region that defines a thickness in the range of from about 0.1 nm to about 10 nm; a pore formed in the first region of the membrane, the pore defining a cross-sectional dimension in the range of from about 0.5 nm to about 5 nm; and a voltage source configured to, during operation, apply a voltage in the range of from about 0.1 V to about 2 V across the pore. Without being bound to any particular theory, applying comparatively large voltages to DNA (or other target molecules) acts to maximally linearize the molecule it and speed up the molecule as it goes to the pore; also reducing any fluctuations of the molecule. This is contrary to the prevailing wisdom in the art, which wisdom suggests that target molecules should be passed comparatively slowly through pores.

Figure 10:
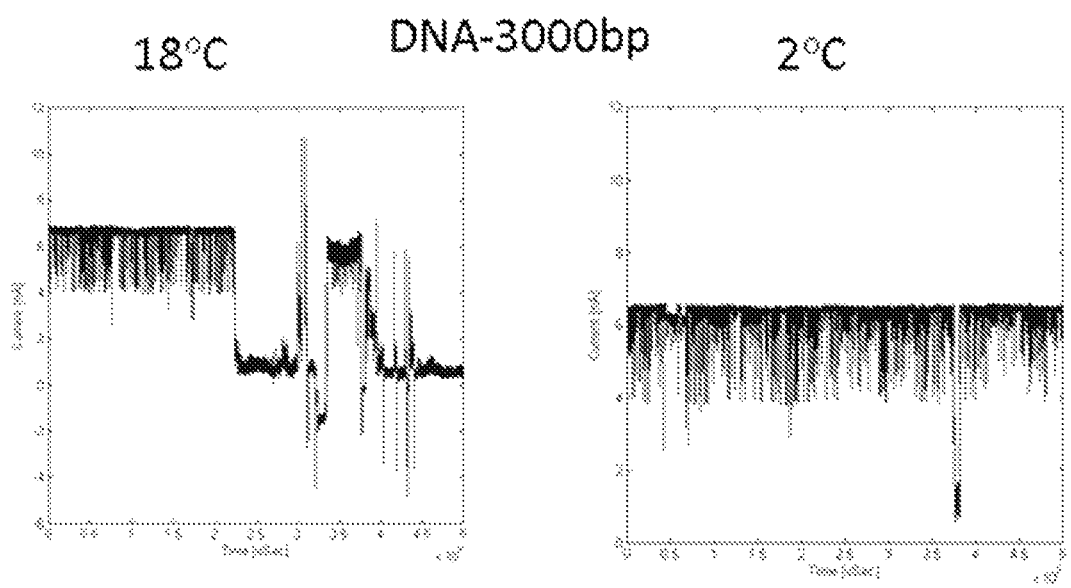
FIG. 10. Measuring at lower temperatures increases the stability of the baseline current and reduces noise in nanopore measurements. In the trace taken at 18 C, the nanopore clogs more frequently and exhibits higher rms noise than in the trace taken at 2 C (~30 pArms at 2 C compared to ~50 pArms at 18 C). Thus, without being bound to any particular theory, noise is lower at lower temperatures.

The systems may also suitably include a device (e.g., a refrigeration coil, a heat sink, a Pelletier cooler, or other cooling device) that is adapted to maintain the temperature in the environment proximate to the pore at less than about 25 deg. C. This may, for example, be accomplished by cooling (e.g., refrigerating) fluid that resides in reservoirs on either side of the pore. The device may, in some embodiments, be adapted to maintain the temperature at around the pore at between about 0 deg. C and about 10 deg. C. FIG. 10 presents exemplary results illustrating the use of reduced temperature.

Membranes may be formed from a variety of materials. Some exemplary—but non-limiting—materials include nitrides (e.g., (SiN, TiN, TaN, WN, NbN, boron nitride (BN), and hexagonal boron nitride). Graphene is also a suitable material, as are metal oxides, such as aluminum oxide ($Al_2O_3$), silicon oxide ($SiO_2$), hafnium oxide ($HfO_2$), titanium oxide ($TiO_2$), and others (e.g., $SnO_2$, ZnO, $SrTiO_3$, $BaTiO_3$, $Bi_2Sr_2CaCu_2O_x$). Sulfides may also be used in membranes; suitable sulfides include $WS_2$, $MoS_2$, $WS_2$, ZnS, and the like. Selenides and tellurides are also suitable membrane materials, some of which include $MoSe_2$, $TaSe_2$, $NbSe_2$, $Bi_2Te_3$, $NiTe_2$, and $MoTe_2$. Metals—including Ru, Ir, and Pt—may also be suitable membrane materials. It should be understood that a membrane may comprise one, two, or more materials in a homogeneous or even in inhomogeneous mixture. Materials that can be deposited in thin layers by atomic-layer deposition methods, materials that can be grown with chemical—vapor deposition method, chemically-functionalized versions of these materials (e.g. graphene coated with hydrophilic molecules), and layered combinations of these materials are all considered suitable.

In some embodiments, the membrane material may be chemically-functionalized or chemically-treated materials above so as to, e.g., increase hydrophillicity, add a specific recognition function to the nanopores, or impart other functionality. Some such exemplary treatments include piranha treatment, acid or base treatment, UV/ozone treatment, plasma treatment, oxidation treatment, reduction treatment, and the like. As one example, SiN may be treated with piranha so as to increase hydrophilicity.

A membrane may include a portion (e.g., a non-thinned portion, or the membrane bulk) that defines a thickness in the range of from about 0.1 nm to about 100 nm, or even in the range of from about 15 nm to about 85 nm. The first region (i.e., the pore-containing region) of the membrane may have a different thickness than the membrane bulk.

The disclosed systems may also include an amplifier in electronic connection with the pore. The system may suitably operate up to about 1 MHz, 50 MHz, 100 MHz, or even about 1000 MHz. A system may also be configured to resolve a signal (e.g., the translocation of a particular target through the pore) of down to about 100 nanosecond temporal resolution, down to about 50 nanosecond temporal resolution, down to about 10 nanosecond temporal resolution or even down to about 1 nanosecond temporal resolution.

A system according to the present disclosure (comprising an amplifier and solid-state chip containing the nanopore) may be configured so as to have a capacitance lower than about 100 pF, lower than about 50 pF, or even lower than about 1 pF, or even less than about 0.1 pF. The system is also suitably configured so as to have a signal-to-noise ratios capable of resolving the internal structure of a biomolecule (e.g., ssDNA). In some embodiments, this means that the system is configured to resolve a current difference (across the pore) of down to about 10 pA, about 5 pA, or 1 pA, or even down to about 0.1 pA. As described elsewhere herein, one may observe differences between nucleic acid bases in the about 100-900 pA range.

The amplifier may also suitably include a filter. The filter may be configured to operate at between about 100 kHz and about 100 MHz, or between about 500 kHz and about 50 MHz, or between about 1 MHz and about 10 MHz. These devices may be constructed by those of ordinary skill in the art and may also be available commercially.

Systems may also be configured such that the pore places first and second reservoirs into fluid communication with one another. In some embodiments, the first reservoir contains biomolecules or other targets disposed in water, a buffer, electrolyte, or other working fluid. The second reservoir may be empty or may contain a fluid.

Pores may be of a variety of configurations. In some embodiments, pores are essentially cylindrical in configuration, having circular openings and a straight (or plumb) inner surface. Pores need not, however, be cylindrical in all configurations. A pore may be characterized as being hourglass-shaped in cross-section. Alternatively, a pore may have a polygonal-shaped opening. Pores may also have sloped, faceted, or curved walls, for example, a hyperbolic-shaped wall.

The voltage source is suitably configured to, during operation, apply a voltage in the range of from about 0.1 V to about 2 V across the pore, or even a voltage of from about 0.5 V to about 0.75 V across the pore. The voltage source may be configured to provide a constant or variable (e.g., sinusoidal) voltage across the pore. The voltage source may be manually controlled or controlled in an automated fashion.

The present disclosure also provides methods of fabricating devices. These methods suitably include ablating material from a membrane so as to form a first thinned region of the membrane; determining (e.g., by current measurement) a first location or several first locations of the thinned region that defines a minimum thickness of the first thinned region; and ablating material at the first location or several first locations of the first thinned region so as to give rise to a pore or array of pores extending through the membrane.

Suitable pores are described elsewhere herein; a pore may define a cross-sectional dimension in the range of from about 0.1 nm to about 5 nm. The thinned region of the membrane suitably defines a thickness of between about 0.1 nm to about 10 nm. It should be understood that the membrane defines a thickness and that the cross-sectional dimension or thickness of the pore may be the same as the membrane thickness but may also differ from the membrane thickness. The actual or active thickness of the pore may be less than the thickness of the membrane, e.g., the thickness of the pore may be a narrow central region of an hourglass-shaped pore that has a thickness that is only some fraction (frequently, about one-third) of the overall membrane thickness.

Ablation may be effected by, e.g., reactive ion etching, plasma etching, electron beam etching and transmission electron beam etching (TEM), focused ion beam (FIB), He ion milling, chemical etching, and the like. Suitable ablation methods are described in, e.g., U.S. patent application Ser. No. 13/587,141.

Current measurement may be performed by sending a beam of particles (e.g., electrons in a transmission electron microscope) through the membrane and measuring this transmitted current at multiple locations on the membrane (e.g., locations within the thinned region of the membrane). Regions that are thicker allow fewer particles (e.g., electrons) to go through and yield a smaller current; similarly, regions that are thinner allow higher transmission of particles through the membrane and yield higher currents. In the TEM example, the transmitted current is directly monitored and can be used to guide the position of the electron beam. By doing so, a user may create a map that shows the through-current at various locations on the membrane— locations that show the highest through-current are the locations that correspond to the thinnest parts of the membrane. The user may then effect further ablation at one of these location to effect pore formation at that location. This can be done by manual control or computer control of the particle beam that will drill the pore. In this way, the user may (1) form a thinned region in a membrane, (2) identify the locations in the thinned region that correspond to the thinnest parts of the thinned region, and (3) form a pore (or pores) at these thinnest parts. One advantage to this technique is that it allows for formation of pores that have the shortest possible thickness, which in turn leads to a pore with greater sensitivity.

This method can proceed after other thinning methods such as reactive ion etching. First, thinning is performed across a larger region with the first thinning method and then it is performed further across a smaller region to achieve nanopore thicknesses down to a single atom thickness. In this way, the membrane area in which the nanopore is drilled can be just slightly larger than the nanopore itself. By this gradual thinning method one ensures the stability and robustness of the whole membrane, in contrast to a situation where a very large thin area is produced, but that makes the membrane much more fragile. A further benefit of thinning across a smallest possible region is that this lowers the chip capacitance and results in lower electronic noise.

In the exemplary TEM approach, the electron beam in the TEM goes through the membrane. The beam impinges on a detector, and one may measure the electron beam current. The user may then measure the number of electrons that go through the membrane per unit area, e.g., measuring the current density in $pA/cm^2$. By moving the beam around, one can obtain different numbers for this beam current. In the scanning TEM mode, the beam is scanned across a sample and can be directed based on the measured currents.

As one non-limiting example, a user might—via ablation—form a thinned region (e.g., about 2 nm to about 10 nm in thickness) in a SiN membrane of 100 nm thickness. The user may then apply the previously-described current map technique to identify the thinnest regions within the thinned region as there are variations in thickness across the thinned region (e.g., there can be a region of 1 nm thickness in a thinned membrane region that was already etched to nominally be 3 nm thick), and may then form pores at those thinnest regions. It is not necessary to know the actual thickness of the thinned region at these minimum-thickness regions. An estimate of the thickness of the resulting nanopore can be later calculated from the measured ionic current through the pore.

The present disclosure also provides methods. These methods suitably include applying a voltage in the range of from about 0.1 V to about 2 V across a pore formed in a membrane, the pore defining a cross-sectional dimension in the range of from about 0.1 nm to about 5 nm, the voltage being applied so as to effect translocation of a molecule through the pore, the temperature at the environment proximate to the pore being between about 0 deg. C and about 25 deg. C.; and monitoring an amplified electronic signal related to the translocation of the molecule.

A user may also correlate the amplified signal to a structural characteristic of the molecule. (Suitable molecules are described elsewhere herein, and include of proteins, RNA, microRNA, DNA, biomarkers, and the like.)

A structural characteristic may be, for example, the presence or absence of a particular nucleic acid. For example, a user may construct a "library" of signals based on collecting signals from known targets. For example, the user may determine that the passage of a cytosine base gives rise to a first type of signal and the passage of a guanine base gives rise to a second type of signal. When passing a target molecule through the pore, the user may then compare the evolved signals to the signals in the library to determine the structure—and sequence—of the target molecule. The structural characteristic may also be, e.g., the sequence (i.e., order) of two or more nucleic acids of the molecule. Correlation may also include comparing amplified signals related to two different locations on the molecule.

An amplified signal may is suitably in the range of from about 100 kHz to about 100 MHz, or from about 500 kHz to about 50 MHz, or even from about 750 kHz to about 1 MHz.

A user may also control the temperature (e.g., in fluid media that contains target molecules) in the area in and around the pore. The temperature may maintained at below 25 degrees C., and may even be maintained between about 0 deg. C. and about 10 deg. C.

Additionally provided are methods that include applying a voltage in the range of from about 0.1 V to about 1.5 V across a pore formed in a membrane, the pore defining a cross-sectional dimension in the range of from about 0.5 nm to about 5 nm, the voltage being applied so as to effect translocation of a molecule through the pore, and; monitoring an amplified electronic signal related to the translocation of the molecule, the signal being in the range of from about 100 kHz to about 100 MHz.

As described elsewhere herein, the user may correlate the amplified signal to a structural characteristic of the molecule; suitable molecules and suitable structural characteristics are also described elsewhere herein. As describe elsewhere herein, An amplified signal may be suitably in the range of from about 100 kHz to about 100 MHz, or from about 500 kHz to about 50 MHz, or even from about 750 kHz to about 1 MHz. A user may also control the temperature (e.g., in fluid media that contains target molecules) in the area in and around the pore. The temperature may maintained at below 25 degrees C., and may even be maintained between about 0 deg. C. and about 10 deg. C.

Additional Disclosure

Described here in further detail are exemplary, non-limiting fabrication and use of 1 to 2-nm-diameter nanopores in 5 to 8-nm-thick silicon nitride (SiN) membranes to measure and characterize ionic current signals obtained by translocating short homopolymers of single-stranded DNA (poly($dA)_{30}$, poly($dC)_{30}$, poly($dT)_{30}$) through these pores. The small nanopore diameter of 1-2 nm is comparable to the width of single-stranded DNA (1.1 nm).

Single-stranded DNA translocations through nanopores of these dimensions result in blockage of ionic current by up to 70-90%, similar to results from protein nanopores. In addition, the reduced nanopore thickness leads to higher ionic conductance, increased bias current, and a reduction in the number of DNA bases present in the nanopore constriction at any moment (approximately 15 bases in a 5 nm thick membrane, see FIG. 1*b*). These highly sensitive $SiN_x$ nanopores are combined with thermoelectric temperature regulation and a custom low-noise amplifier that supports signal bandwidths as high as 1 MHz, which is almost two orders of magnitude faster than most nanopore experiments. This combination of small, thin pores and fast, low-noise electronics allows ionic current measurements to differentiate between short homopolymers.

Figure 1:
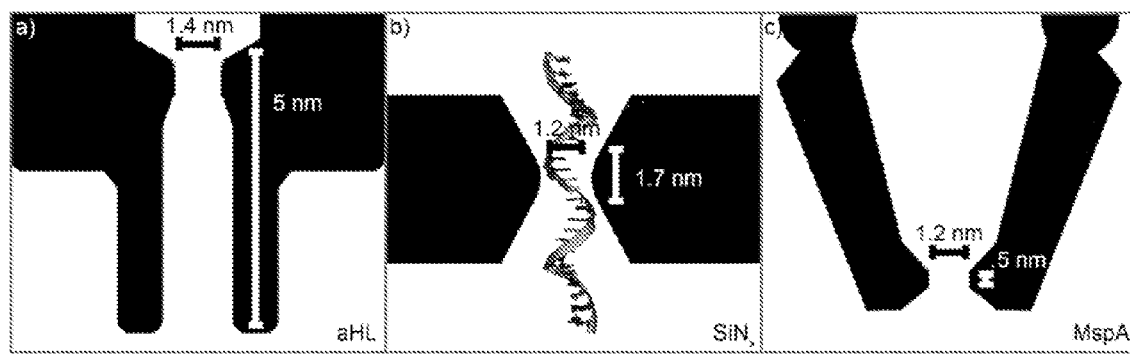
FIG. 1. Comparison of the $SiN_x$ pores presented here to biological pores. All images are on the same scale. (a) biological pore α-hemolysin (aHL) which has a thickness of 5 nm and a diameter of 1.4 nm (b) common dimensions of a $SiN_x$ pore presented here. The pore shown is 1.2 nm in diameter and has an effective thickness ($h_{eff}$) of 1.7 nm in a 5 nm thick membrane. The single-stranded DNA is shown to scale. (c) biological pore MspA which has a thickness of 0.5 nm and a diameter of 1.2 nm.

First compared were dimensions and geometry of biological pores to $SiN_x$ pores. FIGS. 1*a-c* show an illustrated cross-section of a 1.2-nm-diameter pore in a 5-nm-thick SiN$_x$ membrane (FIG. 1b), alongside cross-sections of α-hemolysin (FIG. 1a) and MspA (FIG. 1c) proteins. All three have comparable sizes with small differences in diameter and thickness, as detailed in Table 1. The diameter of the solid-state pores is comparable to both α-hemolysin (1.4 nm) and MspA (1.2 nm), while the thickness is comparable to α-hemolysin (5 nm) but thicker than MspA (0.5 nm). At the same time, one may drill solid-state nanopores even smaller with diameters as small as ~0.8 nm.

While the shape of protein pores is determined by their amino acid sequence and studied using crystallography, the geometry of nanopores in solid-state membranes drilled by transmission electron microscope (TEM) is governed by the interplay between surface tension of the molten SiN$_x$ and its ablation kinetics and can be modified by tuning the electron-beam fabrication process. Based on TEM, ion conductance measurements correlating ion currents to pore sizes, and annular dark field scanning TEM (ADF-STEM) studies, silicon nitride nanopore shapes are known deviate from a perfect cylinder. In fact, electron tomography shows that 7-nm-diameter SiN$_x$ nanopores in a 50-nm-thick membrane have a truncated double-cone or "hourglass" structure. Nevertheless, a simplified geometric model using an equivalent cylinder of reduced effective thickness ($h_{eff}$) and the measured pore diameter is sufficient to quantitatively explain the open and blocked current values measured during DNA translocations. By fitting both the ionic open-pore and blocked-pore current data for many different-diameter pores with the same membrane thickness, $h_{eff}$ is shown to be approximately one-third the actual membrane thickness (h). The exemplary pores presented here in 5-nm-thick SiN$_x$ membranes have $h_{eff}$~1.7 nm. To make a SiN$_x$ effective constriction as thin as the constriction in MspA, a pore would need to be drilled in a region where the SiN$_x$ membrane is about 1.5-nm-thick, giving $h_{eff}$~0.5 nm which measures roughly four DNA bases.

Figure 2:
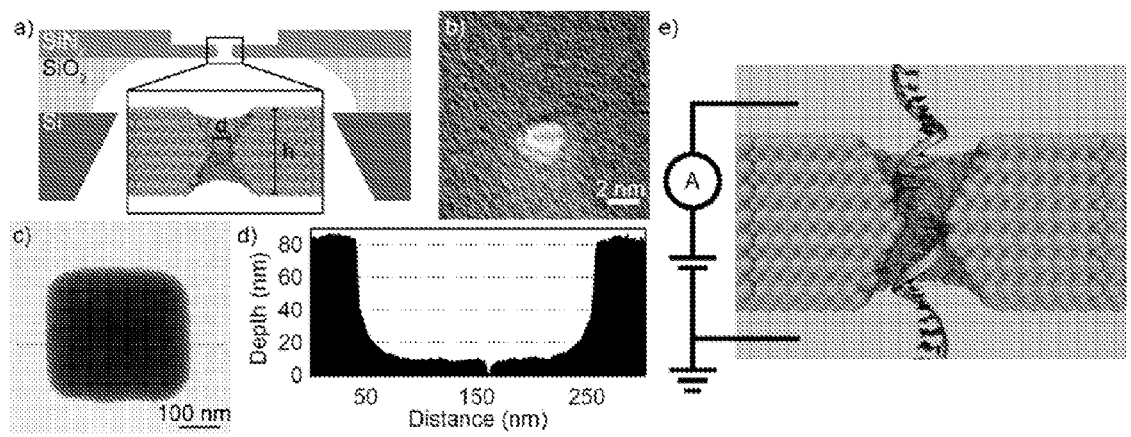
FIG. 2. Device fabrication and characterization, and measurement design. (a) schematic of the stacked silicon chips used to fabricate nanopores. A silicon chip 500 μm thick is coated with 5 μm of silicon dioxide. 85 nm of silicon nitride is then deposited. The chips are etched to create a suspended silicon nitride window. The window is locally thinned and a pore is drilled in it. The pore's height and diameter are defined as shown in the inset. (b) TEM image of a pore drilled in a 5-nm-thick membrane. The pore's diameter is measured from the image to be 1.4 nm. (c) STEM mass contrast image of the thinned region of a membrane with a pore in it. The red line is integrated over to give a profile of the thinned region (d). The mass contrast data is scaled by the known thickness of the original membrane to give the thickness of the thinned region. (e) experimental design. The membrane is positioned to separate two chambers of 1M KCl solution, a bias is applied between the chambers, up to 1V, and the ionic conductance is monitored. As DNA passes through the pore, it blocks a considerable fraction of the pore volume.

FIG. 2a shows the details of a solid-state nanopore design. Nanopore fabrication starts with 10 to 20-micrometer square windows of 85-nm-thick low-stress silicon nitride (SiN$_x$). The SiN$_x$ is supported by a 5×5 mm$^2$ Si chip. Sandwiched between the Si and the SiN$_x$ is a 5-micrometer-thick, thermally-grown SiO$_2$ layer which reduces the membrane capacitance and electrical noise. In order to reduce the nanopore resistance and increase the nanopore sensitivity, one may use a method to obtain sub-10 nm-thick silicon nitride membranes. First, a small region of a freestanding SiN$_x$ membrane supported by a silicon chip is thinned from 85 nm down to the desired thickness, after which a nanopore is fabricated using a TEM Thinning is performed by patterning with electron beam lithography followed by reactive ion etching on a Technics PEII-A plasma etcher. TEM, focused ion beam (FIB), He ion milling, or chemical etching can also be used to reduce the thickness of the SiN$_x$ membrane.

Calibration of the thin pores may be done using the methods developed by Wanunu et al. (Nature Nanotech. 2010). First, squares are patterned and etched to the same size as our thinned nanopore membrane areas for a range of etch times. The absolute etch depth is measured using a Veeco Enviroscope atomic force microscope (AFM). The AFM data is then correlated with the percent of the membrane thickness that was etched, as determined by high-angular ADF-STEM mass contrast images, to give the absolute thickness of the membranes. Thickness error is estimated to be 3 nm due to measurement error and fabrication variation. A typical thinned square mass contrast image is shown in FIG. 2c; the average line intensity profile (in red) gives the mass-thickness contrast shown in FIG. 2d.

Figure 6:
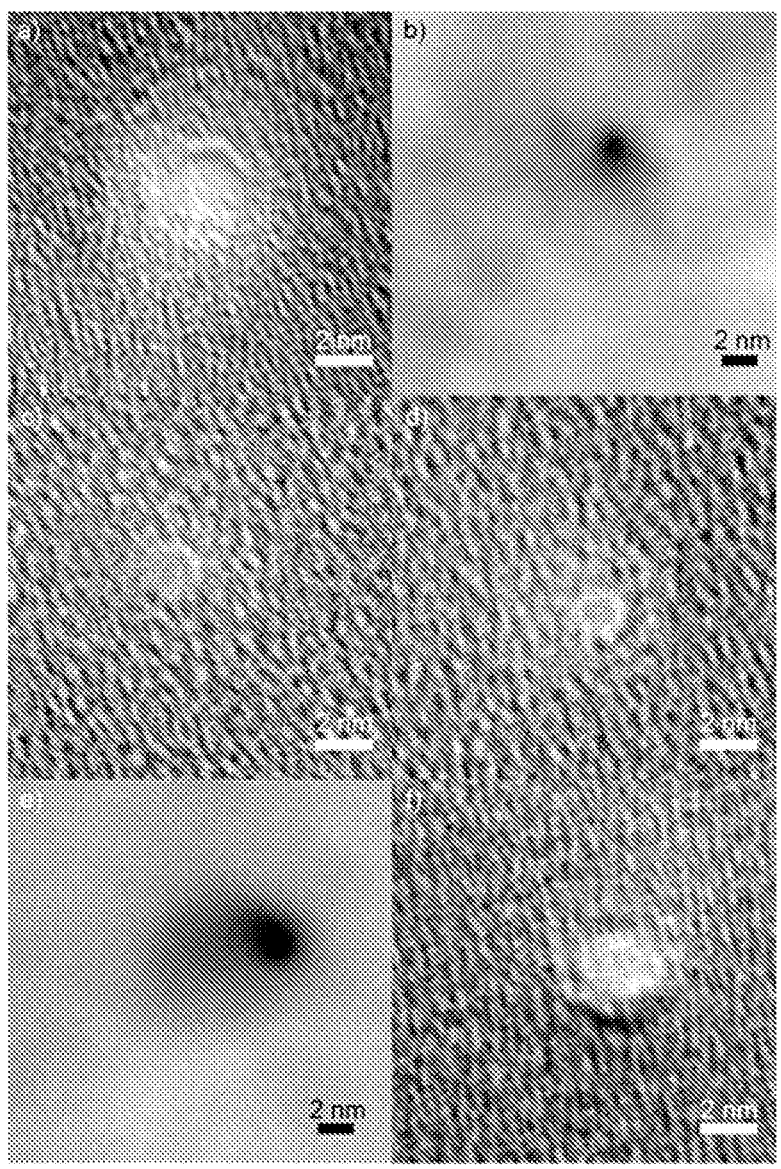
FIG. 6. TEM images of sub-2 nm pores in various thicknesses of SiN$_x$. Most pores fabricated were not imaged to avoid altering the pore size, and many may be smaller than those shown here, based on their appearance while drilling and conductance measurements. Pore diameters from these images are calculated from the average diameter of a fit to an ellipse. (a) 0.9 nm diameter pore in 30 nm thick SiN$_x$ (b) 1.8 nm diameter pore in 5 nm thick SiN$_x$ (c) 1.6 nm diameter pore in 20 nm thick SiN$_x$ (d) 1.3 nm diameter pore in 20 nm thick SiN$_x$ (e) STEM image of a 1.3 nm diameter pore in 8 nm thick SiN$_x$ drilled in a thinner region of the thinned square (f) TEM image of a 2 nm diameter pore in 10 nm thick SiN$_x$.
Figure 7:
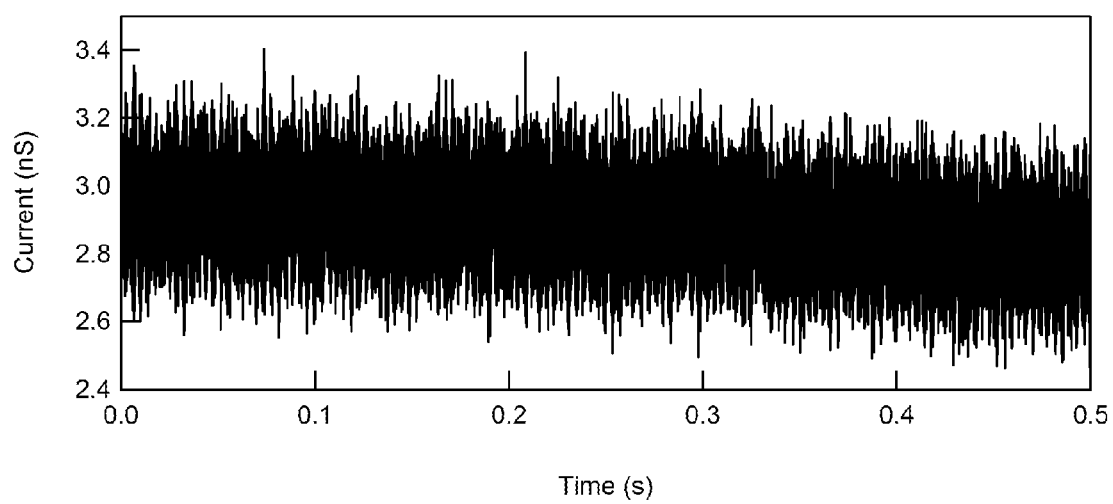
FIG. 7. Ionic current vs time trace for a pore apparently too small to allow translocations. From conductance calculations, we estimate the pore size to be 0.8 nm. This pore was not imaged by TEM to avoid altering its size. The pore has 600 mV applied voltage across it, and approximately 2 µM of an 180mer single-stranded DNA strand in the correct chamber to drive translocations. For over 18 minutes, although the current gradually varied by about 10% (as seen in trace), no translocations were observed, whereas the larger pores readily allowed DNA translocations. Note that the conductance of such small diameter pores in thin membranes is rather high compared to the typical SiN$_x$ pores of the same diameter in much thicker membranes used in most literature.

Nanopores are drilled on a JEOL 2010F TEM set at 200 kV accelerating voltage. Pores are drilled either in TEM mode or in scanning transmission electron microscopy (STEM) mode. FIG. 2b shows an image of a typical pore drilled in TEM mode in a 5-nm-thick membrane (FIG. 6 includes additional pore images). Thin membranes are more easily drilled than the standard 25 to 100-nm-thick membranes, and controlling the pore size to sub-2-nm diameter is achieved with the lowest current densities in the TEM. Most pores presented here are not imaged; one may rely on guides on the TEM screen and calculations from open pore conductance to determine pore size. The conductance measurement approach has the advantage of including size changes that occur with cleaning procedures prior to measurement.

Figure 3:
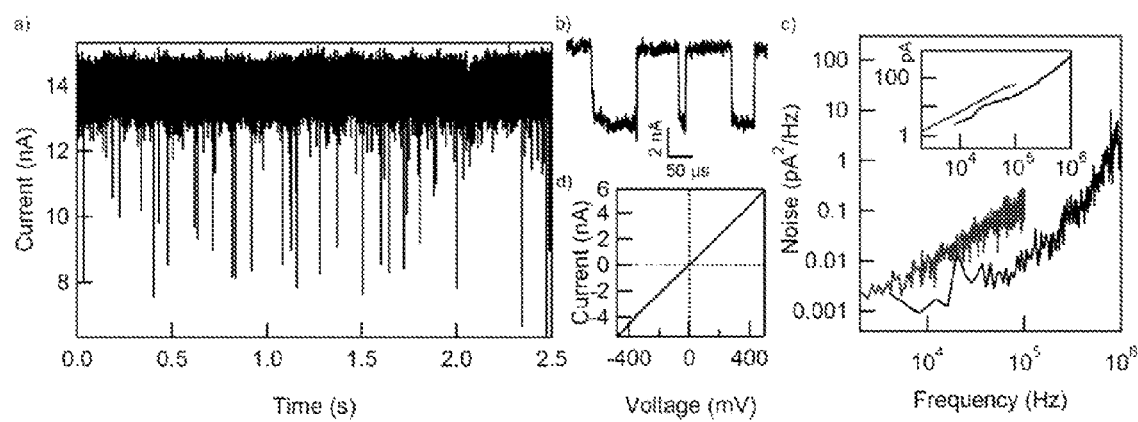
FIG. 3. Characterization of noise in the $SiN_x$ nanopores and the experimental setup using a commercial and custom amplifier. (a) raw current vs. time trace of 50mer single-stranded DNA events in a 2 nm pore in a 5 nm thick membrane with an applied bias of 1 V. Trace is digitally low-pass-filtered to B=1 MHz. (b) zoomed in events from the trace in a. Events have minimal attenuation and high signal-to-noise. (c) input-referred noise power spectral density for a pore measured with an Axopatch 200B (red trace), and a pore measured with the custom amplifier (black trace). Different pores were used for the two measurements, but we found that different pores produce similarly shaped power spectral density curves when they are measured with the same amplifier (see FIG. 8). Inset: integrated noise observed with both amplifiers, as a function of signal bandwidth. This is calculated from the integral of the power spectral density, and it shows the time-domain noise that would be expected after ideal low-pass filtering applied at the given frequency. The x-axis bandwidth is the same scaling as d. (d) Current vs. voltage trace for a 2 nm pore in an 8 nm thick membrane. The slope of the trace gives a conductance of 9.9 nS.

A nanopore device may be cleaned using hot piranha solution followed by repeated water rinsing. The pore is then assembled in a fluoropolymer cell using a homemade quick-cure silicone gasket that divides the cell into two chambers containing a salt solution composed of 1 M KCl+1 mM EDTA buffered to pH 8 using 10 mM Tris-HCl. FIG. 2e shows a schematic of this experimental setup. An exemplary cell may accommodate volumes of 10-50 μL and features temperature regulation using a thermoelectric device connected to a copper block that houses the cell. Data were obtained with the copper block cooled to 2° C. Bias potentials up to 1V are applied across the pore through Ag/AgCl electrodes, and ionic current is monitored as a function of time. When negatively charged DNA molecules are present in the chamber which is at the lower potential, individual DNA translocations through the nanopore appear as transient reductions in the ion current as the DNA displaces ions in the pore, as shown in FIGS. 3a-b. The open pore current in FIG. 3a varies by ~3%.

Experiments were carried out using a custom voltage-clamp amplifier to apply a voltage bias and measure the current through the pore. The custom amplifier was constructed from discrete electronic components, and it extends a traditional patch-clamp circuit topology to support higher signal bandwidths. One may also use an Axopatch 200B (Molecular Devices). The The custom amplifier includes a fourth-order Bessel low-pass filter at 1 MHz, and signals are digitized at 4-6 MS/s. Acquired data are digitally low-pass filtered to the desired signal bandwidth before analysis in Matlab (MathWorks, Natick, Mass.). Not all of the datasets required the full amplifier bandwidth, but higher sample rates ensure many data points per translocation event and provide flexibility during data analysis.

Figure 8:
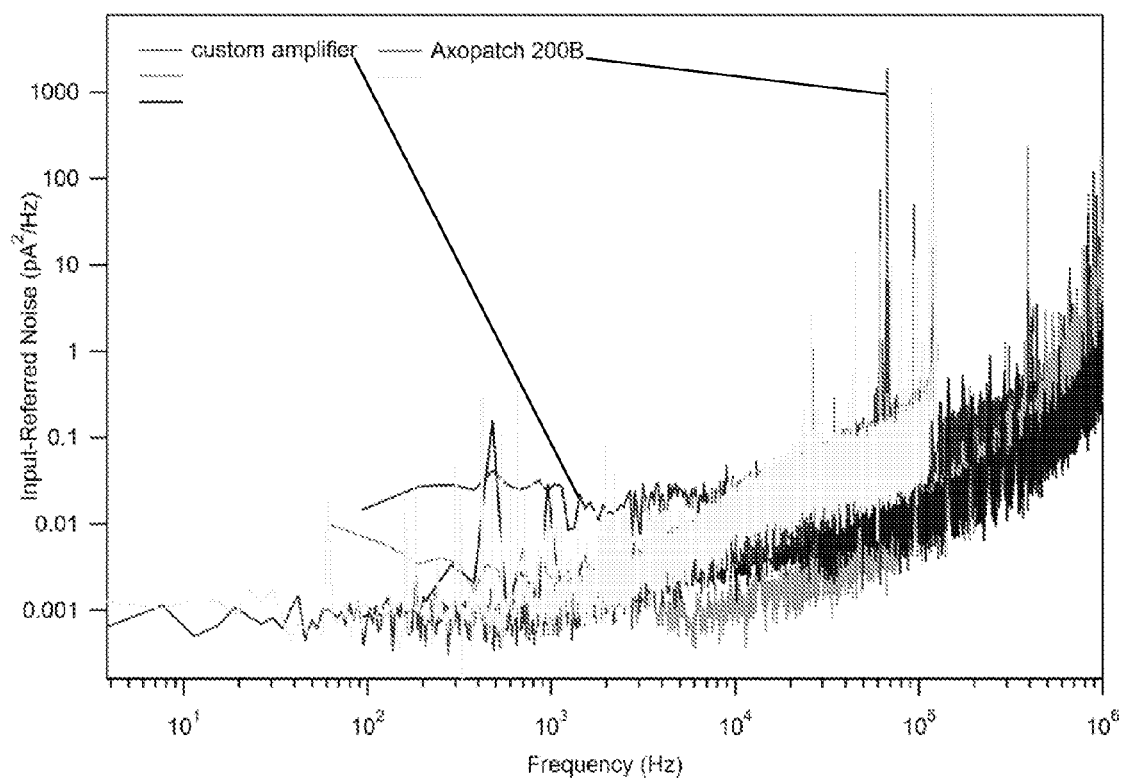
FIG. 8. Input-referred noise of various pores tested on either an Axopatch 200B or our custom amplifier. Although noise from the pore may contribute to these curves, their contribution is largely negligible and the input-referred noise is dominated by the characteristic noise profile of each amplifier.

Pores are found to have a stable current in the absence of DNA, and control experiments are performed to ensure there are no detectable events prior to the addition of ssDNA molecules. Current-voltage traces are obtained before DNA insertion (see FIG. 3c). Ionic conductances extracted from these traces range from 3 nS to 14 nS for pores with diameters between 1 and 2 nm and membrane thicknesses between 5 and 8 nm, matching theoretical predictions. Experiments performed with the custom amplifier generally exhibit less noise than with the Axopatch 200B, as shown in the power spectral densities in FIG. 3d, although there is considerable variance between pores (FIG. 8). Traces typically exhibit input-referred noise of 520 pA$_{rms}$ at the full bandwidth of 1 MHz, and accordingly less noise at lower bandwidths (see FIG. 3c inset). When data are filtered to 100 kHz, a bandwidth closer to many published nanopore recordings, the noise is 24 pA$_{rms}$.

The translocation experiments presented here used 30-base single-stranded DNA composed of homopolymers of either adenine (poly(dA)), thymine (poly(dT)), or cytosine (poly(dC)) (Integrated DNA Technologies). Guanine was not included in these experiments due to G-tetrad formation in homopolymers longer than four bases. Longer single-stranded DNA has been previously measured in solid-state nanopores, but the differences in ionic currents comes primarily from secondary structure in the molecules. This was chosen to be small enough that none of the three homopolymers form such secondary structure. 1 μL of 100 μM solution of one homopolymer is added to the chamber at the lower potential to yield a final concentration of 2 μM. After adding the nucleotides, transient current reductions appear in the ionic-current trace. Between each homopolymer experiment, the pore is rinsed thoroughly with deionized water, and a baseline current trace is recorded for five minutes to ensure that no blockades are seen before the next homopolymer is measured.

Figure 4:
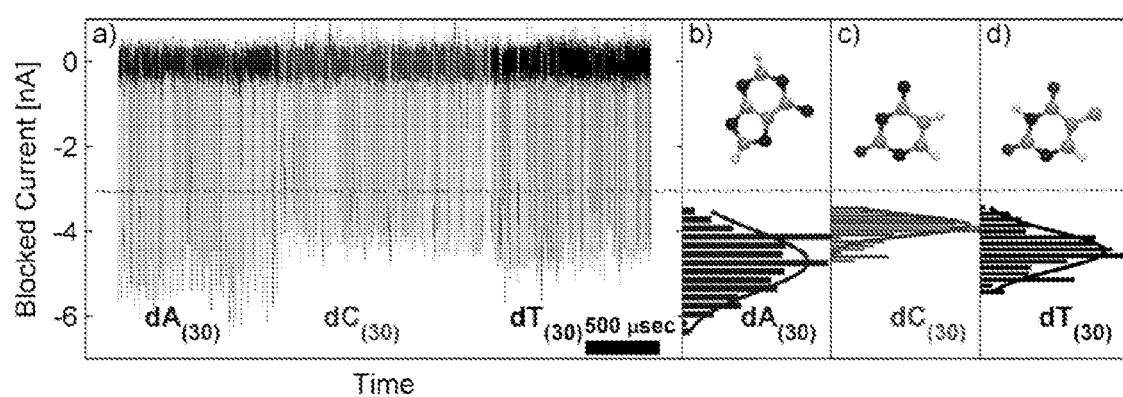
FIG. 4. Results for poly(dA)$_{30}$, poly(dC)$_{30}$, and poly(dT)$_{30}$. (a) concatenated events from each homopolymer with the open pore current subtracted. The green line is the threshold for defining events. (b) normalized histogram of event depths for poly(dA)$_{30}$. The mean value is 5.1±0.4 nA. (c) normalized histogram of event depths for poly(dC)$_{30}$. The mean value is 4.2±0.1 nA. (d) normalized histogram of event depths for poly(dT)$_{30}$. The mean value is 4.8±0.2 nA. Mean values and errors are calculated from Gaussian fits to the histograms. Insets in (b)-(d) are diagrams of the base corresponding to the histogram.
Figure 5:
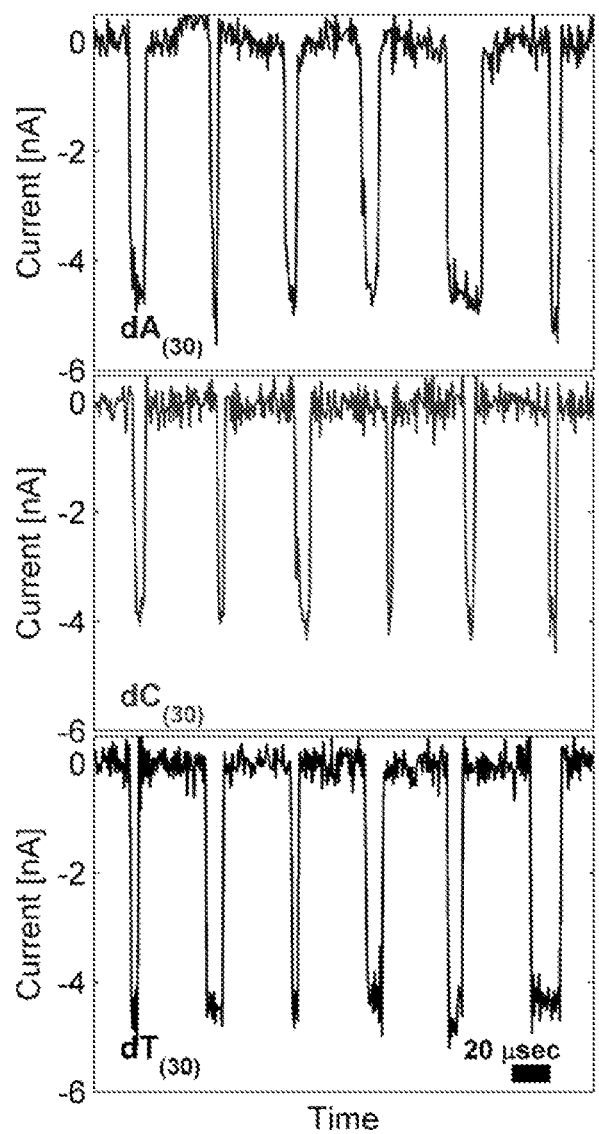
FIG. 5. Sample events from FIG. 4 data set. Top trace (blue) are events from poly(dA)$_{30}$, middle trace (red) are events from poly(dC)$_{30}$, and bottom trace (black) are events from poly(dT)$_{30}$. All open pore currents have been set to zero, and each set has the same y-axis scaling. This data was low-pass filtered to a bandwidth of 500 kHz.

FIG. 4a shows current blockades for each homopolymer, poly(dA)$_{30}$, poly(dC)$_{30}$, and poly(dT)$_{30}$, from a 1.4-nm pore in a 5-nm-thick membrane taken at 1 V applied bias at a signal bandwidth of 500 kHz. The open-pore current has been rescaled to zero and events are identified using a threshold of 3 nA below the open pore current (green line in FIG. 4). FIG. 4a shows ionic current traces containing a large number of short-ssDNA translocation events densely packed in time, such that each event in this figure appears as a narrow spike (the magnified view of these events for each homopolymer is shown in FIG. 5). The current histograms determined from this data for each homopolymer are shown in FIG. 4b-d. Using more than 700 events for each homopolymer, poly(dA)$_{30}$ gave a mean event depth of $<\Delta I_A>=5.1\pm0.4$ nA, poly(dC)$_{30}$ gave a mean event depth of $<\Delta I_C>=4.2\pm0.1$ nA, and poly(dT)$_{30}$ gave a mean event depth of $<\Delta I_T>=4.8\pm0.2$ nA. A Welch's t-test was performed between the event depths of each pair of homopolymers, and the p-value was found to be less than 0.0001 in all three cases, indicating that while the distributions overlap, the difference between the means has strong statistical significance. For the range of pore dimensions presented here, we find the ratios of mean event depths between homopolymers (e.g., $<\Delta I_A>/<\Delta I_C>$) to be consistent. In particular, in three experiments on different pores with pore diameters between 1 and 2 nm and membrane thicknesses between 5 and 8 nm, the ratio of mean event depths of adenine to cytosine is $<\Delta I_A>/<\Delta I_C>=1.25\pm0.05$, the ratio of mean event depths of thymine to cytosine is $<\Delta I_T>/<\Delta I_C>=1.16\pm0.02$, and the ratio of mean event depths of adenine to thymine is $<\Delta I_A>/<\Delta I_T>=1.06$ from a single experiment. The use of these ratios allows for comparison of data collected from different pores.

The current blocked by a homopolymer in the pore is given by $<\Delta I> \sim S/h$, where S is the cross sectional area of the homopolymer and h is the thickness of the nanopore. The ratio of mean currents, therefore, for two homopolymers, for example, poly(dA)$_{30}$ and poly(dC)$_{30}$, is then equal to the ratio of homopolymer cross-sectional areas, $S_A$ and $S_C$, and independent of nanopore thickness, $<\Delta I_A>/<\Delta I_C>=S_A/S_C$. In contrast, other measurements such as the mean current difference (e.g. $<\Delta I_A>-<\Delta I_C> \sim (S_A-S_C)/h$), vary for different nanopores. Without being bound to any theory, the fact that base-pair differentiation is achieved using a range of pore diameters and membrane thicknesses suggests that some geometric variability in solid-state nanopores is tolerable. Since all three homopolymers have the same length (~10 nm), one would expect them to produce similar event durations unless they have different interactions with the pore surfaces. Indeed, poly(dA)$_{30}$ event durations are 17±10 μs, poly(dC)$_{30}$ event durations are 15±10 us, and poly(dT)$_{30}$ event durations are 13±10 μs. These durations are of the same order of magnitude as previous experimental results of 20 μs on double-stranded DNA of similar length (25 base pairs). Mean and error (standard deviations) for both event depth and event duration values are calculated from Gaussian fits to the histograms. Again, without being bound to any particular theory, event duration is clearly not a basis for homopolymer differentiation.

Figure 9:
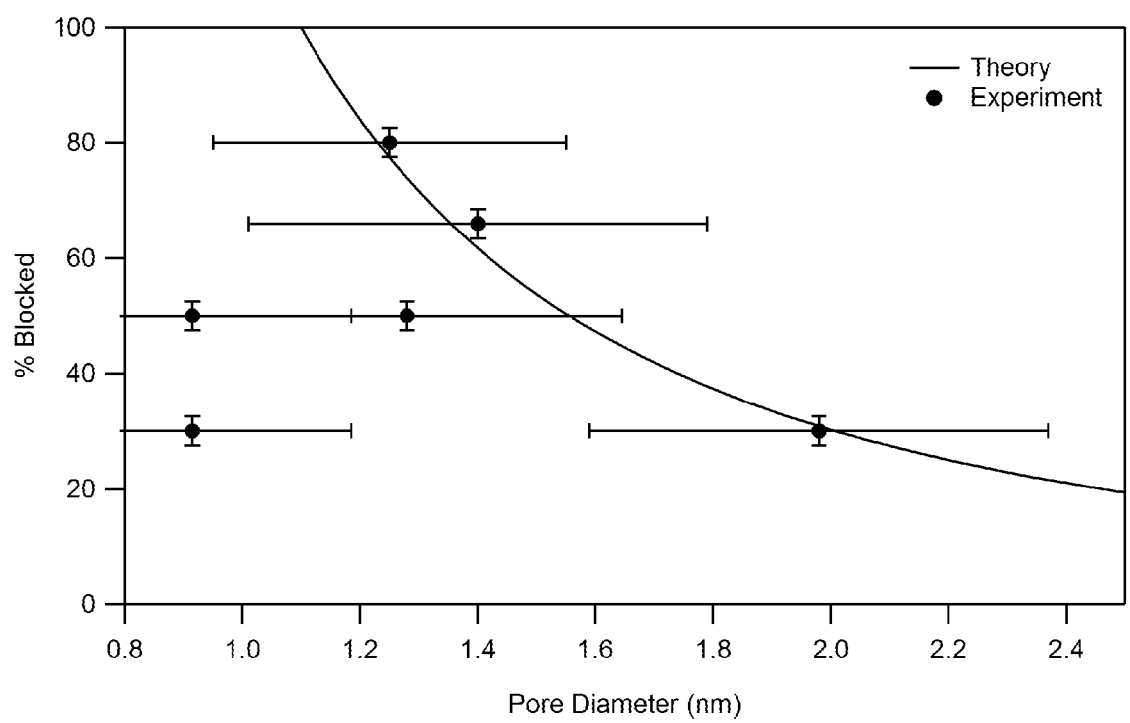
FIG. 9. Percent of the open pore current blocked by homopolymers in six experiments. All pores are between 5 and 10 nm thick, and pore diameter is determined by conductance calculations. The homopolymers used vary by experiment. Theory line, $(1.1)^2/d^2 \times 100\%$, where d is the pore diameter, is a calculation of the percent blocked as determined from the ratio of cross sectional areas of the single stranded DNA and the nanopore.

These results qualitatively fit a model of blockade levels that depends predominantly on the physical size of each base. Adenine, the largest base, blocks the most ionic current, while the two smaller bases (cytosine and thymine) block the least ionic current. The inset of FIGS. 4b-d shows the atomic structure of adenine, cytosine, and thymine Additionally, as observed in FIGS. 4b-d, the width of the current distribution for poly(dA) is larger than the width of the current distributions for poly(dC) and poly(dT). This may be due to the effects of base orientation; the different orientations of the larger adenine base can have a relatively larger effect on the current blockade compared to cytosine and thymine For a range of thin pores with 1 to 2 nm diameters, similar blocked currents are observed for various homopolymers (30-80% of the open pore current) (see FIG. 9), and current differences between pairs of homopolymers are similar to those shown in FIG. 4. Standard deviations in the blockade histograms (FIGS. 4b-d) are comparable to the baseline current noise amplitudes, which suggests that further reduction of measurement noise may reduce the overlap of current distributions between homopolymers.

The examples presented here thus include fabricated solid-state nanopores with diameters as small as ~0.8 nm in membranes as thin as ~5 nm, close in size to commonly-used biological nanopores. Ionic current was measured with improved noise and temporal resolution to demonstrate proof-of-principle differentiation of homopolymer signals. The mean homopolymer current signals measured from several nanopores differ by 200-900 pA in 1M KCl solution at applied voltages between 600 mV and 1 V.

TABLE 1 comparison of physical properties and experimental results between the SiN$_x$ nanopores presented here and two of the most commonly used biological pores: α-hemolysin and MspA.

|  | α-hemolysin (α HL) | MspA | Silicon nitride (SiN$_x$) |
|---|---|---|---|
| Constriction width (nm) | 1.4[59] | 1.2[78] | 1-2 |
| Constriction height (nm) | 5[59] | 0.6[78] | 5-8 |
| Conductance (nS) | 1[5] | 1.8[43] | 3-10 |
| Signal amplitude (nA) | 0.1-0.105[6,29,30,35,36,56] | 0.15-0.26[39,60] | 1-5 |
| Percent of pore blocked | 83-95[6,29,30,35,36,56] | 48-82[39,43,60] | 30-80 |
| Difference in signal between nucleotides (pA) | 5-15[6,35] | 6-11[60] | 300-900 |

What is claimed:
1. A system, comprising:
a membrane having a first region that defines a thickness in the range of from about 0.1 nm to about 10 nm;

a pore formed in the first region of the membrane, the pore defining a cross-sectional dimension in the range of from about 0.1 nm to about 5 nm;

a voltage source configured to, during operation, apply a voltage in the range of from about 0.1 V to about 2 V across the pore; and the system further comprising an amplifier in electronic connection with the pore, the amplifier being configured such that the system is capable of operating at up to about 100 MHz.

2. The system of claim 1, further comprising a device adapted to maintain the temperature in the environment proximate to the pore at less than about 25 deg. C.

3. The system of claim 1, further comprising a species that is more hydrophilic than the membrane, the species surmounting at least a portion of the membrane.

4. The system of claim 1, wherein at least a portion of the membrane defines a thickness in the range of from about 0.1 nm to about 100 nm.

5. The system of claim 1, further comprising an amplifier in electronic connection with the pore, the amplifier being configured such that the system has a capacitance of less than about 50 pico-Farad.

6. The system of claim 1, further comprising an amplifier in electronic connection with the pore, the amplifier being configured such that the system is capable of resolving the internal structure of a biomolecule.

7. The system of claim 1, wherein the amplifier comprises a filter configured to operate at between about 100 kHz and about 100 MHz.

8. A system, comprising:
a membrane having a first region that defines a thickness in the range of from about 0.1 nm to about 10 nm;
a pore formed in the first region of the membrane, the pore defining a cross-sectional dimension in the range of from about 0.1 nm to about 5 nm; and
a voltage source configured to, during operation, apply a voltage in the range of from about 0.1 V to about 2 V across the pore, the system further comprising an amplifier in electronic connection with the pore, the amplifier being configured such that the system is capable of resolving signals down to about 10 nano-second temporal resolution.

9. The system of claim 8, further comprising a device adapted to maintain the temperature in the environment proximate to the pore at less than about 25 deg. C.

10. The system of claim 8, further comprising a species that is more hydrophilic than the membrane, the species surmounting at least a portion of the membrane.

11. The system of claim 8, wherein at least a portion of the membrane defines a thickness in the range of from about 0.1 nm to about 100 nm.

12. The system of claim 8, further comprising an amplifier in electronic connection with the pore, the amplifier being configured such that the system is capable of resolving the internal structure of a biomolecule.

13. The system of claim 8, wherein the amplifier comprises a filter configured to operate at between about 100 kHz and about 100 MHz.

14. The system of claim 8, further comprising an amplifier in electronic connection with the pore, the amplifier being configured such that the system has a capacitance of less than about 50 pico-Farad.

15. A system, comprising:
a membrane having a first region that defines a thickness in the range of from about 0.1 nm to about 10 nm;
a pore formed in the first region of the membrane, the pore defining a cross-sectional dimension in the range of from about 0.1 nm to about 5 nm; and
a voltage source configured to, during operation, apply a voltage in the range of from about 0.1 V to about 2 V across the pore, the system further comprising an amplifier in electronic connection with the pore, the amplifier being configured such that the system is capable of resolving a current difference across the pore of about 0.1 pA.

16. The system of claim 12, further comprising a device adapted to maintain the temperature in the environment proximate to the pore at less than about 25 deg. C.

17. The system of claim 15, further comprising a species that is more hydrophilic than the membrane, the species surmounting at least a portion of the membrane.

18. The system of claim 15, wherein at least a portion of the membrane defines a thickness in the range of from about 0.1 nm to about 100 nm.

19. The system of claim 15, further comprising an amplifier in electronic connection with the pore, the amplifier being configured such that the system is capable of resolving the internal structure of a biomolecule.

20. The system of claim 15, wherein the amplifier comprises a filter configured to operate at between about 100 kHz and about 100 MHz.

21. The system of claim 15, further comprising an amplifier in electronic connection with the pore, the amplifier being configured such that the system has a capacitance of less than about 50 pico-Farad.

* * * * *

UNITED STATES PATENT AND TRADEMARK OFFICE
CERTIFICATE OF CORRECTION

PATENT NO. : 10,017,813 B2
APPLICATION NO. : 14/781453
DATED : July 10, 2018
INVENTOR(S) : Marija Drndic et al.

It is certified that error appears in the above-identified patent and that said Letters Patent is hereby corrected as shown below:

In the Claims

Claim 16, Column 14, at Line 28, delete "claim 12," and insert -- claim 15, --.

Signed and Sealed this
Sixteenth Day of April, 2019

Andrei Iancu
*Director of the United States Patent and Trademark Office*